(12) United States Patent
Soejima et al.

(10) Patent No.: US 7,572,591 B2
(45) Date of Patent: Aug. 11, 2009

(54) CONSTRUCT COMPRISING RECOGNITION DOMAIN OF ANTIBODY AGAINST VON WILLEBRAND FACTOR-SPECIFIC CLEAVING ENZYME

(75) Inventors: Kenji Soejima, Kumamoto (JP); Tomohiro Nakagaki, Kumamoto (JP); Masanori Matsumoto, Nara (JP); Yoshihiro Fujimura, Nara (JP)

(73) Assignee: The Juridical Foundation Chemo-Sero-Therapeutic Research Institute, Kumamoto (JP)

( * ) Notice: Subject to any disclaimer, the term of this patent is extended or adjusted under 35 U.S.C. 154(b) by 62 days.

(21) Appl. No.: 10/549,317

(22) PCT Filed: Mar. 17, 2004

(86) PCT No.: PCT/JP2004/003602

§ 371 (c)(1),
(2), (4) Date: Sep. 16, 2005

(87) PCT Pub. No.: WO2004/083250

PCT Pub. Date: Sep. 30, 2004

(65) Prior Publication Data

US 2006/0240476 A1     Oct. 26, 2006

(30) Foreign Application Priority Data

Mar. 17, 2003   (JP)   .............................. 2003-071979

(51) Int. Cl.
*A61K 38/04*   (2006.01)
*G01N 33/53*   (2006.01)

(52) U.S. Cl. ......................................... 435/7.1; 530/324
(58) Field of Classification Search ....................... None
See application file for complete search history.

(56) References Cited

FOREIGN PATENT DOCUMENTS

| EP | 1 391 516 A1 | 2/2004 |
| EP | 1 544 293 A1 | 6/2005 |
| WO | WO 96/27387 | 9/1996 |

OTHER PUBLICATIONS

Abaza MS, Atassi MZ. Effects of amino acid substitutions outside an antigenic site on protein binding to monoclonal antibodies of predetermined specificity obtained by peptide immunization: demonstration with region 94-100 (antigenic site 3) of myoglobin. Protein Chem. Oct. 1992;11(5):433-44.*
Colman PM. Effects of amino acid sequence changes on antibody-antigen interactions. Res Immunol. 145(1):33-36, 1994.*
Li CH, Yamashiro D, Tseng LF, Chang WC, Ferrar P. beta-Endorphin omission analogs: dissociation of immunoreactivity from other biological activities. Proc Natl Acad Sci U S A. 77(6):3211-3214, 1980.*
Soejima et al. ADAMTS-13 cysteine-rich/spacer domains are functionally essential for von Willebrand factor cleavage. Blood.. Epub Jul. 17, 2003, pp. 1-36.*
Zheng et al. Cleavage of von Willebrand factor requires the spacer domain of the metalloprotease ADAMTS13.:J Biol Chem. Aug. 8, 2003;278(32):30136-41. Epub Jun. 5, 2003.*
Zheng et al. Characterization of Recombinant ADAMTS13 in COS7 cells and Identification of Domains Required for Cleavage of von Willebrand Factor. Bood, (Nov. 16, 2002) vol. 100, No. 11, Abstract No. 974.*
B. Plaimauer et al., "Epitope Mapping of Anti-ADAMTS-13 Antibodies in Patients with Acquired TTP", Blood, Nov. 16, 2003, vol. 102(II), p. 540a.
B. Plaimauer et al., "Cloning, expression, and functional characterization of the von Willebrand factor-cleaving protease (ADAMTS13)" Blood, Nov. 15, 2002, vol. 100(10), pp. 3626-3632.
HE. Gerritsen et al., "Partial amino acid sequence of purified von Willebrand factor-cleaving protease", Blood, Sep. 15, 2001, vol. 98(6), pp. 1654-1661.
CC Huang et al., "Epitope mapping of factor VIII inhibitor antibodies of Chinese origin.", Br. J. Haematol., Jun. 2001, vol. 113(4), pp. 915-924.
MA Nardi et al., "GPIIIa- (49-66) is a major pathaophysiologically relevant antigenic determinant for anti-platelet GPIIIa of HIV-1-related immunologic thrombocytopenia.", Proc. Natl. Acad. Sci. USA, Jul. 8, 1997, vol. 94(14), pp. 7589-7594.
K. Kokame et al., "Mutations and common polymorphisms in ADAMTS13 gene responsible for von Willebrand factor-cleaving protease activity", Proc. Natl. Acad. Sci. USA, Sep. 3, 2002, vol. 99(18), pp. 11902-11907.
S. Cal et al., "Cloning, expression analysis, and structural characterization of seven novel human ADAMSs, a family of metalloproteinases with disintegrin and thrombospondin-1 domains.", Gene, Jan. 23, 2002, vol. 283 (1-2), pp. 49-62.
Kenji Soejima et al., "A Noel Human Metalloprotease Synthesized in the Liver and Secreted into the Blood: Possibly the von Willebrand Factor-Cleaving Protease", J. Biochem. 130, 475-480, 2001.
Kenji Soejima et al., "Analysis on the Molecular Species and Concentration of Circulating ADAMTS13 in Blood", J. Biochem, 139, 147-154, 2006.
Xinglong Zheng et al., "Structure of von Willebrand Factor-cleaving Protease (ADAMTS13), a Metalloprotease Involved in Thrombotic Thrombocytopenic Purpura", The Journal of Biological Chemistry, vol. 276, No. 44, Issue of Nov. 2, 2001, pp. 41059-41063.

* cited by examiner

*Primary Examiner*—Maher M Haddad
(74) *Attorney, Agent, or Firm*—Stephen A. Bent; Foley & Lardner LLP (57) ABSTRACT

The present invention provides an epitope recognized by an antibody (hereinafter, also referred to as an anti-ADAMTS-13 antibody) against a cleaving protease (hereinafter, also referred to as ADAMTS-13) specific to von Willebrand factor (hereinafter, also referred to as vWF), and a polypeptide comprising the epitope region. The present invention also provides a polypeptide located in a region from position 449 to position 687 in an amino acid sequence composing the ADAMTS-13, which is recognized by the anti-ADAMTS-13 antibody, or a peptide fragment derived from the polypeptide.

4 Claims, 7 Drawing Sheets
(5 of 7 Drawing Sheet(s) Filed in Color)

1. Normal IgG
2. Anti-FLAG M2 MoAb
3. Patient 003 IgG
4. Patient 004 IgG
5. Patient 009 IgG ← Full-length ← W688stop 1. Patient 003 IgG with Q449 sup
2. Patient 003 IgG with W688 sup
3. Patient 003 IgG with Full sup
4. Patient 004 IgG with Q449 sup
5. Patient 004 IgG with W688 sup
6. Patient 004 IgG with Full sup
7. Patient 009 IgG with Q449 sup
8. Patient 009 IgG with W688 sup
9. Patient 009 IgG with Full sup

SEQUENCE LISTING

```
<160> NUMBER OF SEQ ID NOS: 21

<210> SEQ ID NO 1
<211> LENGTH: 1427
<212> TYPE: PRT
<213> ORGANISM: Homo sapiens

<400> SEQUENCE: 1

Met His Gln Arg His Pro Arg Ala Arg Cys Pro Pro Leu Cys Val Ala
 1               5                  10                  15

Gly Ile Leu Ala Cys Gly Phe Leu Leu Gly Cys Trp Gly Pro Ser His
            20                  25                  30

Phe Gln Gln Ser Cys Leu Gln Ala Leu Glu Pro Gln Ala Val Ser Ser
        35                  40                  45
```

-continued

```
Tyr Leu Ser Pro Gly Ala Pro Leu Lys Gly Arg Pro Pro Ser Pro Gly
     50                  55                  60

Phe Gln Arg Gln Arg Gln Arg Arg Ala Ala Gly Gly Ile Leu
 65                  70                  75                  80

His Leu Glu Leu Leu Val Ala Val Gly Pro Asp Val Phe Gln Ala His
                 85                  90                  95

Gln Glu Asp Thr Glu Arg Tyr Val Leu Thr Asn Leu Asn Ile Gly Ala
            100                 105                 110

Glu Leu Leu Arg Asp Pro Ser Leu Gly Ala Gln Phe Arg Val His Leu
        115                 120                 125

Val Lys Met Val Ile Leu Thr Glu Pro Glu Gly Ala Pro Asn Ile Thr
    130                 135                 140

Ala Asn Leu Thr Ser Ser Leu Leu Ser Val Cys Gly Trp Ser Gln Thr
145                 150                 155                 160

Ile Asn Pro Glu Asp Asp Thr Asp Pro Gly His Ala Asp Leu Val Leu
                165                 170                 175

Tyr Ile Thr Arg Phe Asp Leu Glu Leu Pro Asp Gly Asn Arg Gln Val
            180                 185                 190

Arg Gly Val Thr Gln Leu Gly Gly Ala Cys Ser Pro Thr Trp Ser Cys
        195                 200                 205

Leu Ile Thr Glu Asp Thr Gly Phe Asp Leu Gly Val Thr Ile Ala His
    210                 215                 220

Glu Ile Gly His Ser Phe Gly Leu Glu His Asp Gly Ala Pro Gly Ser
225                 230                 235                 240

Gly Cys Gly Pro Ser Gly His Val Met Ala Ser Asp Gly Ala Ala Pro
                245                 250                 255

Arg Ala Gly Leu Ala Trp Ser Pro Cys Ser Arg Arg Gln Leu Leu Ser
            260                 265                 270

Leu Leu Ser Ala Gly Arg Ala Arg Cys Val Trp Asp Pro Pro Arg Pro
        275                 280                 285

Gln Pro Gly Ser Ala Gly His Pro Pro Asp Ala Gln Pro Gly Leu Tyr
    290                 295                 300

Tyr Ser Ala Asn Glu Gln Cys Arg Val Ala Phe Gly Pro Lys Ala Val
305                 310                 315                 320

Ala Cys Thr Phe Ala Arg Glu His Leu Asp Met Cys Gln Ala Leu Ser
                325                 330                 335

Cys His Thr Asp Pro Leu Asp Gln Ser Ser Cys Ser Arg Leu Leu Val
            340                 345                 350

Pro Leu Leu Asp Gly Thr Glu Cys Gly Val Glu Lys Trp Cys Ser Lys
        355                 360                 365

Gly Arg Cys Arg Ser Leu Val Glu Leu Thr Pro Ile Ala Ala Val His
    370                 375                 380

Gly Arg Trp Ser Ser Trp Gly Pro Arg Ser Pro Cys Ser Arg Ser Cys
385                 390                 395                 400

Gly Gly Gly Val Val Thr Arg Arg Gln Cys Asn Asn Pro Arg Pro
                405                 410                 415

Ala Phe Gly Gly Arg Ala Cys Val Gly Ala Asp Leu Gln Ala Glu Met
            420                 425                 430

Cys Asn Thr Gln Ala Cys Glu Lys Thr Gln Leu Glu Phe Met Ser Gln
        435                 440                 445

Gln Cys Ala Arg Thr Asp Gly Gln Pro Leu Arg Ser Ser Pro Gly Gly
    450                 455                 460

Ala Ser Phe Tyr His Trp Gly Ala Ala Val Pro His Ser Gln Gly Asp
```

-continued

|     | 465 |     |     |     | 470 |     |     |     | 475 |     |     |     | 480 |     |     |
|-----|-----|-----|-----|-----|-----|-----|-----|-----|-----|-----|-----|-----|-----|-----|-----|

Ala Leu Cys Arg His Met Cys Arg Ala Ile Gly Glu Ser Phe Ile Met
                    485                 490                 495

Lys Arg Gly Asp Ser Phe Leu Asp Gly Thr Arg Cys Met Pro Ser Gly
            500                 505                 510

Pro Arg Glu Asp Gly Thr Leu Ser Leu Cys Val Ser Gly Ser Cys Arg
            515                 520                 525

Thr Phe Gly Cys Asp Gly Arg Met Asp Ser Gln Gln Val Trp Asp Arg
        530                 535                 540

Cys Gln Val Cys Gly Gly Asp Asn Ser Thr Cys Ser Pro Arg Lys Gly
545                 550                 555                 560

Ser Phe Thr Ala Gly Arg Ala Arg Glu Tyr Val Thr Phe Leu Thr Val
                565                 570                 575

Thr Pro Asn Leu Thr Ser Val Tyr Ile Ala Asn His Arg Pro Leu Phe
            580                 585                 590

Thr His Leu Ala Val Arg Ile Gly Gly Arg Tyr Val Val Ala Gly Lys
        595                 600                 605

Met Ser Ile Ser Pro Asn Thr Thr Tyr Pro Ser Leu Leu Glu Asp Gly
    610                 615                 620

Arg Val Glu Tyr Arg Val Ala Leu Thr Glu Asp Arg Leu Pro Arg Leu
625                 630                 635                 640

Glu Glu Ile Arg Ile Trp Gly Pro Leu Gln Glu Asp Ala Asp Ile Gln
                645                 650                 655

Val Tyr Arg Arg Tyr Gly Glu Glu Tyr Gly Asn Leu Thr Arg Pro Asp
            660                 665                 670

Ile Thr Phe Thr Tyr Phe Gln Pro Lys Pro Arg Gln Ala Trp Val Trp
        675                 680                 685

Ala Ala Val Arg Gly Pro Cys Ser Val Ser Cys Gly Ala Gly Leu Arg
    690                 695                 700

Trp Val Asn Tyr Ser Cys Leu Asp Gln Ala Arg Lys Glu Leu Val Glu
705                 710                 715                 720

Thr Val Gln Cys Gln Gly Ser Gln Gln Pro Ala Trp Pro Glu Ala
                725                 730                 735

Cys Val Leu Glu Pro Cys Pro Pro Tyr Trp Ala Val Gly Asp Phe Gly
            740                 745                 750

Pro Cys Ser Ala Ser Cys Gly Gly Gly Leu Arg Glu Arg Pro Val Arg
        755                 760                 765

Cys Val Glu Ala Gln Gly Ser Leu Leu Lys Thr Leu Pro Pro Ala Arg
    770                 775                 780

Cys Arg Ala Gly Ala Gln Gln Pro Ala Val Ala Leu Glu Thr Cys Asn
785                 790                 795                 800

Pro Gln Pro Cys Pro Ala Arg Trp Glu Val Ser Glu Pro Ser Ser Cys
                805                 810                 815

Thr Ser Ala Gly Gly Ala Gly Leu Ala Leu Glu Asn Glu Thr Cys Val
            820                 825                 830

Pro Gly Ala Asp Gly Leu Glu Ala Pro Val Thr Glu Gly Pro Gly Ser
        835                 840                 845

Val Asp Glu Lys Leu Pro Ala Pro Glu Pro Cys Val Gly Met Ser Cys
    850                 855                 860

Pro Pro Gly Trp Gly His Leu Asp Ala Thr Ser Ala Gly Glu Lys Ala
865                 870                 875                 880

Pro Ser Pro Trp Gly Ser Ile Arg Thr Gly Ala Gln Ala Ala His Val
                885                 890                 895

-continued

Trp Thr Pro Ala Ala Gly Ser Cys Ser Val Ser Cys Gly Arg Gly Leu
                900                 905                 910

Met Glu Leu Arg Phe Leu Cys Met Asp Ser Ala Leu Arg Val Pro Val
                915                 920                 925

Gln Glu Glu Leu Cys Gly Leu Ala Ser Lys Pro Gly Ser Arg Arg Glu
                930                 935                 940

Val Cys Gln Ala Val Pro Cys Pro Ala Arg Trp Gln Tyr Lys Leu Ala
945                 950                 955                 960

Ala Cys Ser Val Ser Cys Gly Arg Gly Val Val Arg Arg Ile Leu Tyr
                965                 970                 975

Cys Ala Arg Ala His Gly Glu Asp Gly Glu Glu Ile Leu Leu Asp
                980                 985                 990

Thr Gln Cys Gln Gly Leu Pro Arg Pro Glu Pro Gln Glu Ala Cys Ser
                995                 1000                1005

Leu Glu Pro Cys Pro Pro Arg Trp Lys Val Met Ser Leu Gly Pro Cys
                1010                1015                1020

Ser Ala Ser Cys Gly Leu Gly Thr Ala Arg Arg Ser Val Ala Cys Val
1025                1030                1035                1040

Gln Leu Asp Gln Gly Gln Asp Val Glu Val Asp Glu Ala Ala Cys Ala
                1045                1050                1055

Ala Leu Val Arg Pro Glu Ala Ser Val Pro Cys Leu Ile Ala Asp Cys
                1060                1065                1070

Thr Tyr Arg Trp His Val Gly Thr Trp Met Glu Cys Ser Val Ser Cys
                1075                1080                1085

Gly Asp Gly Ile Gln Arg Arg Arg Asp Thr Cys Leu Gly Pro Gln Ala
                1090                1095                1100

Gln Ala Pro Val Pro Ala Asp Phe Cys Gln His Leu Pro Lys Pro Val
1105                1110                1115                1120

Thr Val Arg Gly Cys Trp Ala Gly Pro Cys Val Gly Gln Gly Thr Pro
                1125                1130                1135

Ser Leu Val Pro His Glu Glu Ala Ala Ala Pro Gly Arg Thr Thr Ala
                1140                1145                1150

Thr Pro Ala Gly Ala Ser Leu Glu Trp Ser Gln Ala Arg Gly Leu Leu
                1155                1160                1165

Phe Ser Pro Ala Pro Gln Pro Arg Arg Leu Leu Pro Gly Pro Gln Glu
                1170                1175                1180

Asn Ser Val Gln Ser Ser Ala Cys Gly Arg Gln His Leu Glu Pro Thr
1185                1190                1195                1200

Gly Thr Ile Asp Met Arg Gly Pro Gly Gln Ala Asp Cys Ala Val Ala
                1205                1210                1215

Ile Gly Arg Pro Leu Gly Glu Val Val Thr Leu Arg Val Leu Glu Ser
                1220                1225                1230

Ser Leu Asn Cys Ser Ala Gly Asp Met Leu Leu Leu Trp Gly Arg Leu
                1235                1240                1245

Thr Trp Arg Lys Met Cys Arg Lys Leu Leu Asp Met Thr Phe Ser Ser
                1250                1255                1260

Lys Thr Asn Thr Leu Val Val Arg Gln Arg Cys Gly Arg Pro Gly Gly
1265                1270                1275                1280

Gly Val Leu Leu Arg Tyr Gly Ser Gln Leu Ala Pro Glu Thr Phe Tyr
                1285                1290                1295

Arg Glu Cys Asp Met Gln Leu Phe Gly Pro Trp Gly Glu Ile Val Ser
                1300                1305                1310

Pro Ser Leu Ser Pro Ala Thr Ser Asn Ala Gly Gly Cys Arg Leu Phe
        1315                1320                1325

Ile Asn Val Ala Pro His Ala Arg Ile Ala Ile His Ala Leu Ala Thr
1330                1335                1340

Asn Met Gly Ala Gly Thr Glu Gly Ala Asn Ala Ser Tyr Ile Leu Ile
1345                1350                1355                1360

Arg Asp Thr His Ser Leu Arg Thr Thr Ala Phe His Gly Gln Gln Val
                1365                1370                1375

Leu Tyr Trp Glu Ser Glu Ser Gln Ala Glu Met Glu Phe Ser Glu
            1380                1385                1390

Gly Phe Leu Lys Ala Gln Ala Ser Leu Arg Gly Gln Tyr Trp Thr Leu
        1395                1400                1405

Gln Ser Trp Val Pro Glu Met Gln Asp Pro Gln Ser Trp Lys Gly Lys
        1410                1415                1420

Glu Gly Thr
1425

<210> SEQ ID NO 2
<211> LENGTH: 30
<212> TYPE: DNA
<213> ORGANISM: Homo sapiens

<400> SEQUENCE: 2
ctggagcacg acggcgcgcc cggcagcggc                              30

<210> SEQ ID NO 3
<211> LENGTH: 30
<212> TYPE: DNA
<213> ORGANISM: Homo sapiens

<400> SEQUENCE: 3
atgtgcaaca ctcaggcctg cgagaagacc                              30

<210> SEQ ID NO 4
<211> LENGTH: 30
<212> TYPE: DNA
<213> ORGANISM: Homo sapiens

<400> SEQUENCE: 4
ccaacctgac cagtgtctac attgccaacc                              30

<210> SEQ ID NO 5
<211> LENGTH: 21
<212> TYPE: DNA
<213> ORGANISM: Homo sapiens

<400> SEQUENCE: 5
ctggagccct gcccacctag g                                       21

<210> SEQ ID NO 6
<211> LENGTH: 62
<212> TYPE: DNA
<213> ORGANISM: Homo sapiens

<400> SEQUENCE: 6
tccgtcgact cttatcactt atcgtcatcg tccttgtagt cgtcccacac gcagcgcgcc    60
cg                                                                  62

<210> SEQ ID NO 7
<211> LENGTH: 62

<212> TYPE: DNA
<213> ORGANISM: Homo sapiens

<400> SEQUENCE: 7
tccgtcgact cttatcactt atcgtcatcg tccttgtagt cgcgcccatg cactgctgct     60
at                                                                    62

<210> SEQ ID NO 8
<211> LENGTH: 62
<212> TYPE: DNA
<213> ORGANISM: Homo sapiens

<400> SEQUENCE: 8
gccgtcgact cttatcactt atcgtcatcg tccttgtagt cttgcgacat gaactccagc     60
tg                                                                    62

<210> SEQ ID NO 9
<211> LENGTH: 62
<212> TYPE: DNA
<213> ORGANISM: Homo sapiens

<400> SEQUENCE: 9
gccgtcgact cttatcactt atcgtcatcg tccttgtagt ccaggttggg ggtaactgtc     60
ag                                                                    62

<210> SEQ ID NO 10
<211> LENGTH: 62
<212> TYPE: DNA
<213> ORGANISM: Homo sapiens

<400> SEQUENCE: 10
tccgtcgact cttatcactt atcgtcatcg tccttgtagt ccacccaggc ctgccgtggc     60
tt                                                                    62

<210> SEQ ID NO 11
<211> LENGTH: 62
<212> TYPE: DNA
<213> ORGANISM: Homo sapiens

<400> SEQUENCE: 11
tccgtcgact cttatcactt atcgtcatcg tccttgtagt cgtagggagg gcagggttcg     60
ag                                                                    62

<210> SEQ ID NO 12
<211> LENGTH: 62
<212> TYPE: DNA
<213> ORGANISM: Homo sapiens

<400> SEQUENCE: 12
tccgtcgact cttatcactt atcgtcatcg tccttgtagt ccctggcagg gcagggctgg     60
gg                                                                    62

<210> SEQ ID NO 13
<211> LENGTH: 62
<212> TYPE: DNA
<213> ORGANISM: Homo sapiens

<400> SEQUENCE: 13
gccgtcgact cttatcactt atcgtcatcg tccttgtagt ccacgtgtgc agcttgagcc     60

-continued

```
cc                                                             62

<210> SEQ ID NO 14
<211> LENGTH: 62
<212> TYPE: DNA
<213> ORGANISM: Homo sapiens

<400> SEQUENCE: 14
gccgtcgact cttatcactt atcgtcatcg tccttgtagt ccctaggtgg gcagggctcc    60
ag                                                             62

<210> SEQ ID NO 15
<211> LENGTH: 62
<212> TYPE: DNA
<213> ORGANISM: Homo sapiens

<400> SEQUENCE: 15
gccgtcgact cttatcactt atcgtcatcg tccttgtagt caccctgtcc cacacagggc    60
cc                                                             62

<210> SEQ ID NO 16
<211> LENGTH: 60
<212> TYPE: DNA
<213> ORGANISM: Homo sapiens

<400> SEQUENCE: 16
tccaagcttg tcgactctta tcacttatcg tcatcgtcct tgtagtcggt tccttccttt    60

<210> SEQ ID NO 17
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
gactacaagg acgatgacga taagtga                                  27

<210> SEQ ID NO 18
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Asp Tyr Lys Asp Asp Asp Asp Lys
 1               5

<210> SEQ ID NO 19
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Arg Gln Arg Arg
 1

<210> SEQ ID NO 20
```

-continued

```
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide consensus sequence
<220> FEATURE:
<221> NAME/KEY: MOD_RES
<222> LOCATION: (3)..(4)
<223> OTHER INFORMATION: variable amino acid
<220> FEATURE:
<221> NAME/KEY: MOD_RES
<222> LOCATION: (6)..(7)
<223> OTHER INFORMATION: variable amino acid
<220> FEATURE:
<221> NAME/KEY: MOD_RES
<222> LOCATION: (9)..(10)
<223> OTHER INFORMATION: variable amino acid

<400> SEQUENCE: 20

His Glu Xaa Xaa His Xaa Xaa Gly Xaa Xaa His Asp
  1               5                  10

<210> SEQ ID NO 21
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Arg Gly Asp Ser
  1
```

CONSTRUCT COMPRISING RECOGNITION DOMAIN OF ANTIBODY AGAINST VON WILLEBRAND FACTOR-SPECIFIC CLEAVING ENZYME

TECHNICAL FIELD

The present invention relates to the field of ethical drugs. Specifically, the present invention relates to an epitope recognized by an antibody (hereinafter, also referred to as an anti-ADAMTS-13 antibody) against cleaving protease (hereinafter, also referred to as ADAMTS-13) specific to von Willebrand factor (hereinafter, also referred to as vWF) involved in blood coagulation, and to a polypeptide comprising the epitope region. The present invention is also relates to an antibody that recognizes the polypeptide.

The polypeptide or a peptide fragment thereof provided by the present invention, which comprises an epitope region recognized by an antibody against ADAMTS-13 opens up the possibility of diagnosis given on the presence or absence of an autoantibody against ADAMTS-13 or an absorbing agent for the autoantibody or ADAMTS-13 replacement therapy for a patient with diseases associated with positivity for the autoantibody.

BACKGROUND ART vWF is a blood coagulation factor that is produced in a vascular endothelial cell and a megakaryocyte and is present as a multimer structure (with a molecular weight of 500 to 20,000 kDa) where single subunits each composed of 2050 amino acid residues (approximately 250-kDa monomers) are bound through a S—S bond. The concentration of vWF in blood is approximately 10 μg/ml, and in general, vWF with a higher molecular weight has higher specific activity.

The vWF has two major functions as a blood coagulation factor, one of which is a function as a carrier protein that binds to and thereby stabilizes blood coagulation factor VIII and another of which is a function of helping platelets adhere and aggregate to the tissue beneath vascular endothelial cells of injured vascular walls to form platelet thrombi.

Thrombotic thrombocytopenic purpura (hereinafter, also referred to as TTP) is a disease that causes platelet thrombi in body tissue arterioles and capillary vessels in the whole body. In spite of the current progression of medical technology, the mortality associated with the disease has increased approximately threefold from 1971 to 1991. Pathologically, the TTP is considered to be caused by vascular endothelia cell injury and platelet aggregation in blood vessels. Immunohistologically, the presence of vWF in large amounts is observed in generated platelet thrombi, and the vWF is considered to play a crucial role in the pathogenesis of the disease. TTP is broadly divided into familial (congenital) TTP likely to have an inheritance factor and acquired (idiopathic) TTP developed especially in adults. Normal or high-molecular-weight vWF multimer structures are dominant in TTP patients. Especially, unusually large vWF multimer (ULvWFM) and large vWF multimer (LvWFM) are presumed to play a crucial role in the promotion of platelet aggregation and microthrombus formation under high shearing stress. On the other hand, vWF has been known to undergo digestion at the location between 842Tyr and 843Met by the action of vWF-cleaving protease under high shearing stress in circulating blood of healthy individuals. Thus, a probable scenario of how TTP is caused is as follows: the activity of the protease in plasma is reduced for some reason and ULvWFM or LvWFM is increased to accelerate platelet aggregation, followed by platelet thrombus formation in the blood vessel.

In 2001, a gene encoding vWF-cleaving protease also known as ADAMTS-13 that is an active body having the activity of the protease described above was cloned by the present inventors (JP Patent Publication (Kokai) No. 2003-284570). The findings about the molecular structure of ADAMTS-13 are summarized below. The location of a residue number that is numbered from methionine encoded by an initiation codon (ATG) is shown as a rough guide within parentheses (see SEQ ID No. 1).

The domain structure of ADAMTS-13 has a signal peptide preceding a propeptide that ends in a RQRR (SEQ ID NO: 19) sequence as a furin cleavage motif, followed by a metalloprotease domain containing a reprolysin-type zinc-chelating region consisting of HEXXHXXGXXHD (SEQ ID NO: 20) as a consensus sequence (to amino acid residue No. 284 (p285X)); via a disintegrin-like domain as found in snake venom metalloprotease (to amino acid residue No. 386 (W387X)), there exists a first Tspl motif (Tspl-1) consisting of approximately 50 to 60 residues generally considered to be important for molecular recognition (to amino acid residue No. 448 (Q449X)), which continues to a Cys-rich region containing a RGDS (SEQ ID NO: 21) sequence as one of cell adhesion motifs (to amino acid residue No. 580 (T581X)); and, through a spacer domain consisting of approximately 130 amino acid residues with no cysteine residue (to amino acid residue No. 687 (W688X)), additional Tspl motif repeats (Tspl-2 to Tspl-8) follow, which is followed by a CUB domain-1, and -2 that are said to be first found in a complement component C1r or C1s.

By the way, no finding about a major neutralizing epitope region in ADAMTS-13 has been obtained so far. In addition, a convenient diagnostic method for a patient positive for an autoantibody against the protease has not been established.

In light of such circumstances, a first object of the present invention is directed to an invention relating to the identification of a neutralizing epitope present on ADAMTS-13 and a neutralizing/absorbing agent for an antibody thereby proposed, which is mainly intended for an autoantibody.

A second object of the present invention is to provide a method of producing the neutralizing/absorbing agent.

A third object of the present invention is to provide an application of the neutralizing/absorbing agent.

A fourth object of the present invention is to provide a method of producing a full-length or partially modified molecule of vWF-specific cleaving protease, which is obtained by modifying the epitope.

A fifth object of the present invention is to provide an application of the full-length or partially modified molecule of vWF-specific cleaving protease, which is obtained by modifying the epitope.

Up to now, plasmapheresis has been provided as treatment to a patient congenitally deficient in vWF-specific cleaving protease and a patient with acquired production of an antibody against the protease. Therefore, there is a demand for the establishment of replacement therapy with pure vWF-specific cleaving protease such as the protease purified or genetically altered. It has been reported that a familial TTP patient is congenitally deficient in vWF-specific cleaving protease and non-familial TTP is caused by the acquired production of an autoantibody against the protease. Thus, replacement therapy with the protease is preferred for a familial TTP patient (in reality, plasma administration is given to the patient), while a non-familial TTP patient requires the removal of an autoantibody by plasma exchange as well as the supplementation of the protease.

However, in the administration of ADAMTS-13 for supplementation to a patient positive for an autoantibody, an antibody against the protease, that is, an autoantibody, present in blood of the patient neutralizes the administered protease. As a result, the protease loses enzyme activity and has substantial reduction in concentration. However, the use of a neutralizing region identified by a method of determining an epitope for an antibody against ADAMTS-13 disclosed in a previous application (JP Patent Application No. 2002-279924) or identified by the present invention as well as the preparation of a partially modified molecule of a neutralizing epitope region that can be newly identified by Western blotting of competitive inhibition assay used in the present invention allows the administration of the protease to a patient positive for an antibody against the protease; or alternatively, allows the absorption of the antibody by a polypeptide or the like containing the neutralizing region provided by the present invention.

DISCLOSURE OF THE INVENTION

As a result of conducting diligent studies for attaining the isolation and identification of vWF-cleaving protease under the above-described circumstances, the present inventors successfully purified and isolated heretofore unreported vWF-cleaving protease of interest and identified an amino acid sequence of a mature protein thereof and a gene encoding the amino acid sequence in the previous application (JP Patent Publication (Kokai) No. 2003-284570).

Based on the findings obtained using genetic recombination techniques described in the previous application (JP Patent Publication (Kokai) No. 2003-284570), the present inventors identified a region likely to be essential for activity expression (JP Patent Application No. 2002-279924). From the results of using a mutant molecule prepared on the basis of these findings to analyze a major neutralizing region recognized by an autoantibody against anti-ADAMTS-13 in an acquired TTP patient in the present invention, it has been revealed that the region recognized by the autoantibody is in agreement with the above-described region likely to be essential for activity expression and is located in a region from a Cys-rich region (at approximately position 499) to a spacer region (at approximately position 687). Accordingly, a principal requirement of a major neutralizing epitope region provided by the present invention for an anti-ADAMTS-13 antibody is the region from the Cys-rich region (at approximately position 499) to the spacer region (at approximately position 687) in a polypeptide composing ADAMTS-13 or a peptide fragment having an equivalent amino acid sequence. That is, the present invention relates to a polypeptide comprising a neutralizing epitope region in von Willebrand factor-specific cleaving protease (hereinafter, also referred to as vWFCP or ADAMTS-13), which is recognized by an antibody against the protease, or a peptide fragment derived from the polypeptide. The neutralizing epitope region in the polypeptide or the peptide fragment derived from the polypeptide that is claimed in claim 1 is located in a region from position 449 to position 687 in an amino acid sequence shown in SEQ ID No. 1. The present invention is further intended to a polypeptide comprising an amino acid sequence from position 449 to position 687 in an amino acid sequence shown in SEQ ID No. 1, or a peptide fragment derived from the polypeptide. The present invention is also intended to a polypeptide comprising an amino acid sequence from position 449 to position 687 in an amino acid sequence shown in SEQ ID No. 1 where one or several amino acids are deleted, substituted, or added, the polypeptide being recognized by an antibody against von Willebrand factor-specific cleaving protease, or a peptide fragment derived from the polypeptide. One or several amino acids used herein refers to one to five amino acids, preferably one to three amino acids, more preferably one or two amino acids.

Using, as an antigen, a polypeptide or the like of the neutralizing epitope region, which is prepared on the basis of the amino acid sequence of ADAMTS-13 obtained by this finding, for example, monoclonal and polyclonal antibodies can be created by a typical immunization method (Current Protocols in Molecular Biology, edited by F. M. Ausbel et al., (1987); Antibody Engineering: A PRACTICAL APPROACH, edited by J. McCAFFERTY et al., (1996); Antibodies: A Laboratory Manual, edited by Harlow David Lane (1988); or ANTIBODY ENGINEERING second edition, edited by Carl A. K. BORREBAECK (1995)). Alternatively, an antibody binding to the protein (ADAMTS-13) can be created by a technique of creating an antibody by use of a phage display technique (Phage Display of Peptides and Proteins: A Laboratory Manual, edited by Brian K. Kay et al., (1996); Antibody Engineering: A PRACTICAL APPROACH, edited by J. McCAFFERTY et al., (1996); or ANTIBODY ENGINEERING second edition, edited by Carl A. K. BORREBAECK (1995)). Based on these techniques, a neutralizing antibody for the activity of the protease of the present invention or an antibody simply binding to the protease can also be isolated from a sample from a TTP patient positive for an autoantibody against the protease of the present invention. In addition, the use of these antibodies allows the application of the present invention to diagnosis and treatment for a disease associated with variations in the amount of the protease of the present invention, for example, TTP. The present invention also encompasses these antibodies.

In one embodiment, the present invention relates to a method of diagnosing a patient with a TTP-like disease or a patient at risk of developing vWF-dependent thrombosis, and the method comprises steps below.

Diagnostic assay for a disease associated with variations in the amount of the protease of the present invention is performed using a biological sample from the patient. Such a sample can be used directly in the assay or, in some cases, can need to be subjected prior to the assay to treatment such as the removal of possible interfering substances in the sample. Examples of suitable biological samples include blood, urine, sweat, tissue, or serum. The method involves detecting an autoantibody against vWF-cleaving protease in the biological sample. The steps of the method are as follows:

(a) bringing a biological sample obtained from the patient into contact with a solid support in which ADAMTS-13 or a partial peptide fragment thereof is immobilized;

(b) bringing the solid support into contact with an anti-human immunoglobulin antibody labeled with a developer; and (c) detecting the label of the specifically bound developer in the step (b) in order to obtain a value corresponding to the concentration of an anti-ADAMTS-13 antibody in the sample.

The above-described diagnosis can be conducted by immunoassay known in the art. Solid supports that can be used include beads and plates made of a resin such as polystyrene. Developers that can be used include radioisotopes, enzymes such as peroxidase and alkaline phosphatase, and fluorescent substances.

In an alternative embodiment of the present invention, the polypeptide of the present invention is also useful as a neutralizing agent for an autoantibody by administering the polypeptide to a patient positive for an anti-ADAMTS-13 antibody or as a removing agent for an autoantibody. In this case, the neutralization of the autoantibody refers to binding to the autoantibody, thereby inhibiting the binding of the autoantibody to vWF-cleaving protease. In this method, the polypeptide is optionally immobilized in a suitable support or the like using a method known in the art. Subsequently, a sample containing an anti-ADAMTS-13 antibody to be removed, for example, blood from the patient is brought into contact with the immobilized polypeptide to thereby remove the autoantibody from the sample from the patient. On this occasion, a carrier bound with a ligand specific to the anti-ADAMTS-13 antibody is brought into contact with blood or plasma from the patient and the anti-ADAMTS-13 antibody in the blood or the plasma is bound to the ligand to thereby remove the antibody from the blood or the plasma. Subsequently, the blood or the plasma from which the antibody have been removed may be reinjected to the patient. The above-described polypeptide or peptide fragment derived from the polypeptide can be used as the ligand specific to the anti-ADAMTS-13 antibody. The contact may be performed, for example, by allowing the blood or plasma from the patient to pass through the carrier bound with the ligand. The present invention further encompasses a method of producing blood or plasma free from an anti-ADAMTS 13 antibody by bringing a carrier bound with the above-described polypeptide or peptide fragment derived from the polypeptide into contact with blood or plasma from a patient positive for an anti-ADAMTS-13 antibody and binding an anti-ADAMTS-13 antibody in the blood or the plasma to the ligand to remove the antibody from the blood or the plasma.

A neutralizing agent for an autoantibody administered to a patient positive for an anti-ADAMTS-13 antibody is a pharmaceutical composition for treating a patient positive for an anti-ADAMTS-13 antibody comprising, as an active ingredient, the above-described polypeptide or peptide fragment derived from the polypeptide. The pharmaceutical composition for treating a patient positive for an anti-ADAMTS-13 antibody also includes a pharmaceutical composition for treating a patient positive for an anti-ADAMTS-13 antibody comprising, as an active ingredient, a polypeptide or a peptide fragment derived from the polypeptide composed of the above-described polypeptide or peptide fragment derived from the polypeptide, which lacks reactivity with an anti-ADAMTS-13 antibody by modification such as molecular substitution, deletion, or insertion. The modification such as molecular substitution, deletion, or insertion used herein refers to the deletion, substitution, or addition of one or several amino acids, for example, in an amino acid sequence of the above-described polypeptide or peptide fragment derived from the polypeptide. Such modification allows, for example, alteration in the structure of the polypeptide or the peptide fragment and therefore allows the loss of the epitope. Accordingly, the polypeptide or the peptide fragment loses reactivity with the anti-ADAMTS-13 antibody. When the polypeptide of the present invention recognized by an ADAMTS-13 antibody is used, for example, as a neutralizing agent for an autoantibody by administering the polypeptide to a patient positive for an anti-ADAMTS-13 antibody, the polypeptide can be diluted with a saline, a buffer solution, or the like, and made into a preparation to obtain a pharmaceutical composition. The pH of the preparation is preferably in the pH range from weakly-acidic pH to neutral pH, which is close to body fluid pH; a lower limit thereof is preferably from pH 5.0 to 6.4 and an upper limit thereof is preferably from pH 6.4 to 7.4. The preparation can also be provided in a form storable for a long period such as a freeze-dried form. In this case, when used, the preparation can be dissolved in water, a saline, a buffer solution, or the like, and then used at a desired concentration. The preparation of the present invention may contain pharmacologically acceptable additives (e.g., carriers, excipients, and diluents) and stabilizers that are usually used in drugs or other ingredients that are pharmaceutically required. The stabilizers are exemplified by monosaccharides such as glucose, disaccharides such as saccharose and maltose, sugar alcohols such as mannitol and sorbitol, neutral salts such as sodium chloride, amino acids such as glycine, nonionic surfactants such as polyethylene glycol, a polyoxyethylene-polyoxypropylene copolymer (Pluronic), and polyoxyethylene sorbitan fatty acid ester (Tween), and human albumin. It is preferred that any of these stabilizers on the order of 1 to 10 w/v % should be added to the preparation.

The pharmaceutical composition of the present invention can be administered in an effective amount by, for example, intravenous injection, intramuscular injection, or subcutaneous injection and is administered in a single dosage or several dosages. The dosage varies depending on the symptom, age, body weight, and so on, of a patient and is preferably 0.001 mg to 100 mg per dosage.

The present specification encompasses contents described in the specification and/or drawings of JP Patent Application No. 2003-071979 that serves as a basis for the priority of the present application.

BRIEF DESCRIPTION OF THE DRAWINGS

This application file contains at least one drawing executed in color. Copies of this patent or patent application publication with color drawing(s) will be provided by the Office upon request and payment of the necessary fee.

BEST MODE FOR CARRYING OUT THE INVENTION

Although the present invention will be described hereinafter in detail with reference to Examples, the present invention is not intended to be limited to these Examples by any means.

EXAMPLES

Preparation Example 1

Preparation of C-terminus Deletion Mutant of ADAMTS-13

Figure 1A:
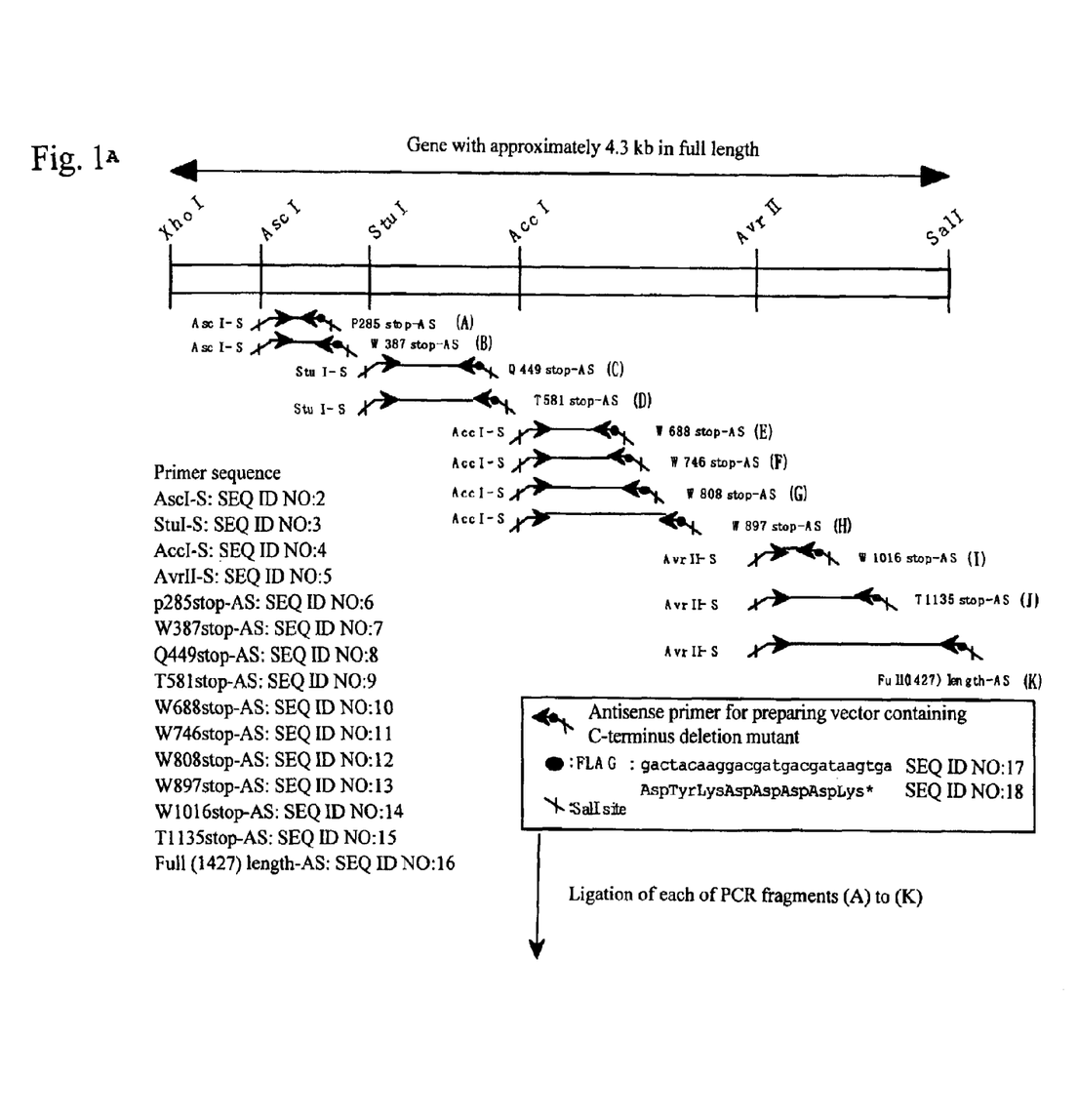
FIG. 1A-1B is a diagram showing a method of producing a C-terminus deletion mutant for determining an epitope for an antibody.
Figure 1B:
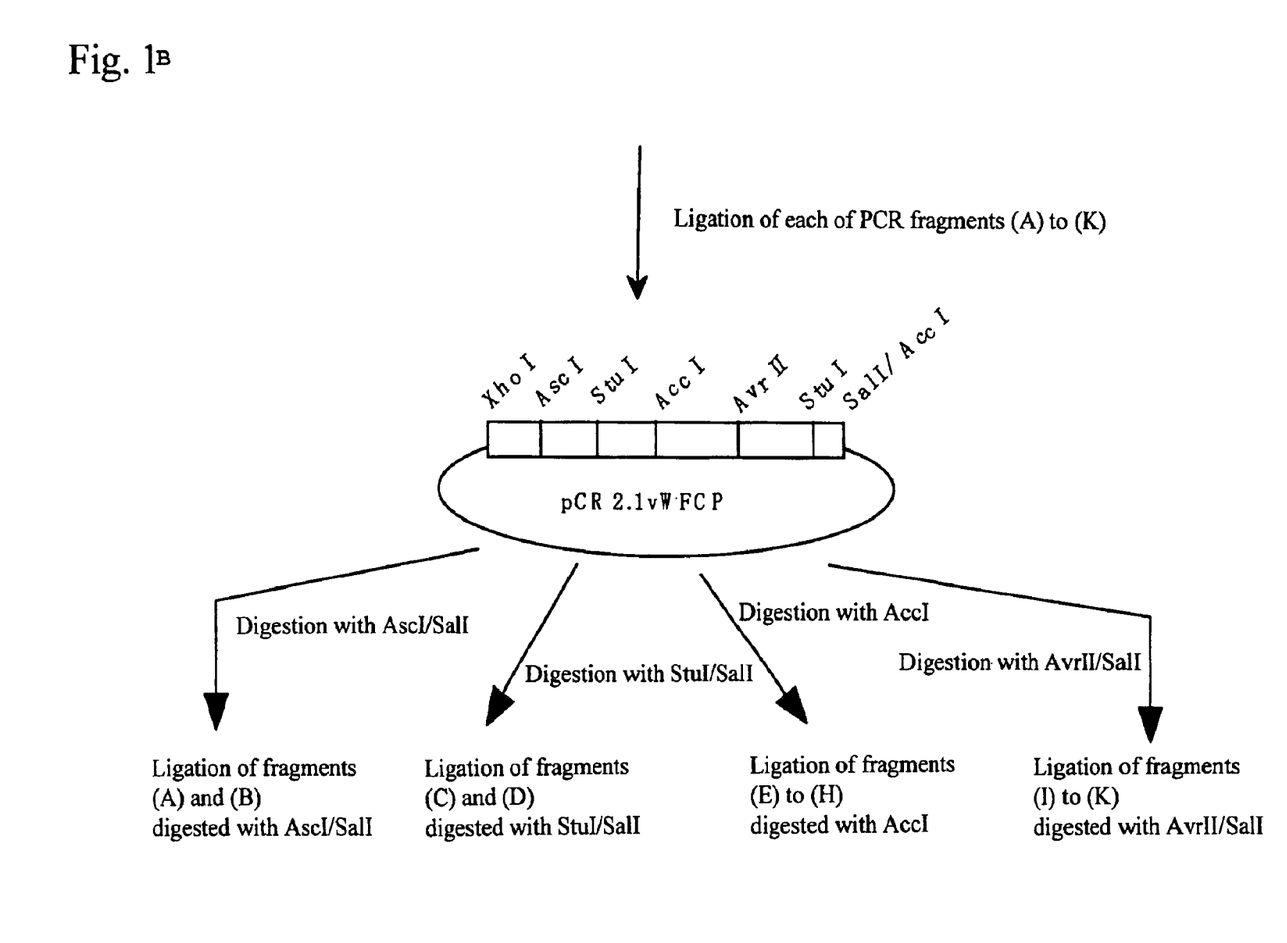

Expression vectors for full-length and mutant (sequentially lacking domains from the C terminus) (Fu1427, and T1135X, W1016X, W897X, W808X, W746X, W688X, T581X, Q449X, W387X, and P285X; each numerical value represents the number of amino acid residues from Met encoded by an initiation codon ATG to a stop codon, and X represents a stop codon) genes described in the previous patent application (JP Patent Application No. 2002-279924) were utilized to perform transfection using Hela cells in the procedures below. Each mutant location in a full-length sequence is shown in FIG. 1.

Figure 2:
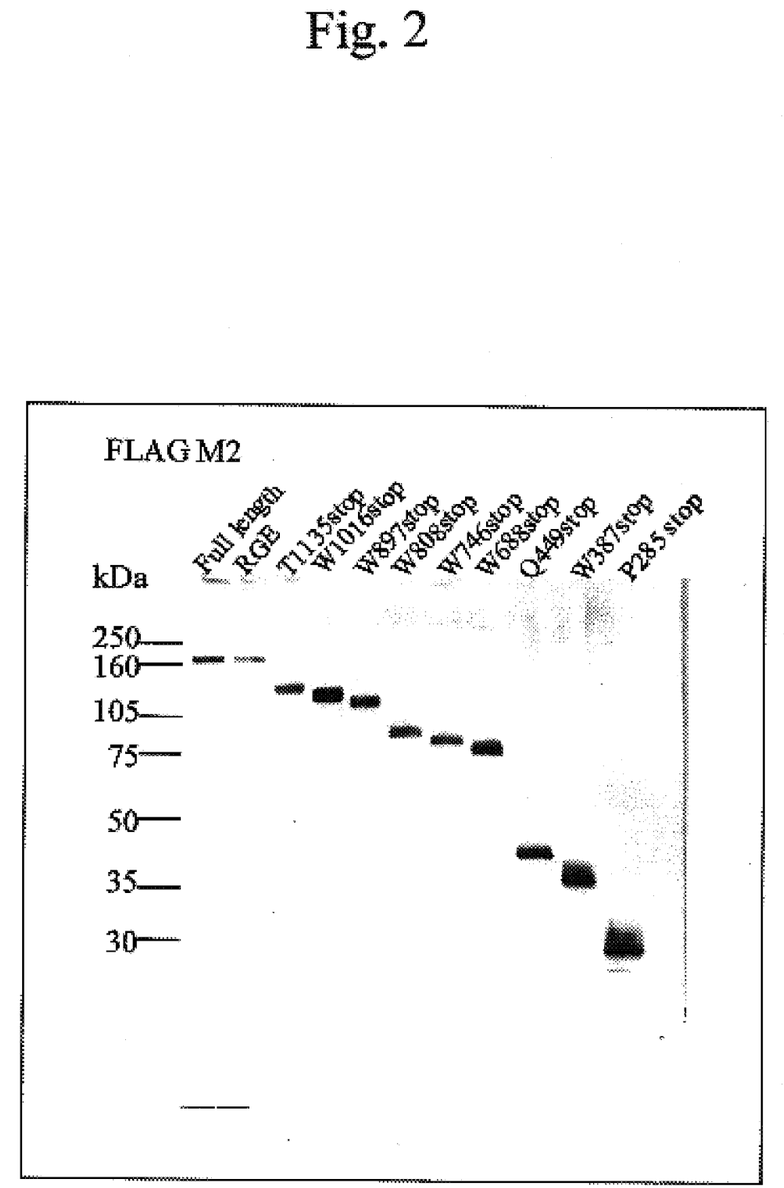
FIG. 2 is a photograph in which the expression and abundance of the prepared C-terminus deletion mutant has been confirmed by Western blotting under non-reducing conditions using an anti-FLAG antibody.

At first, 24 hours before transfection, $1\text{-}3\times10^5$ cells per 35-mm dish were seeded. On the following day, 10 µl of the Polyamine Transfection Reagent TransIT (manufactured by TAKARA) per 2 µg of each of the expression vectors was added to 200 µl of a serum-free medium such as Opti-MEM to prepare a complex with DNA according to the instructions attached to the reagent. The complex was then added dropwise to the above-described various cells prepared in advance and was incubated for 6 hours. Seventy-two hours after the incubation, the medium was collected. The detection of each appropriately concentrated mutant was conducted Western blotting using an anti-FLAG-M2 antibody (manufactured by Kodak) and staining with an anti-mouse IgG-alkaline phosphatase enzyme-labeled antibody system (the result of confirming the expression of the mutants is shown in FIG. 2).

Example 1

Analysis of Epitope for Antibody in Acquired TTP Patient Using Western Blotting

Figure 3:
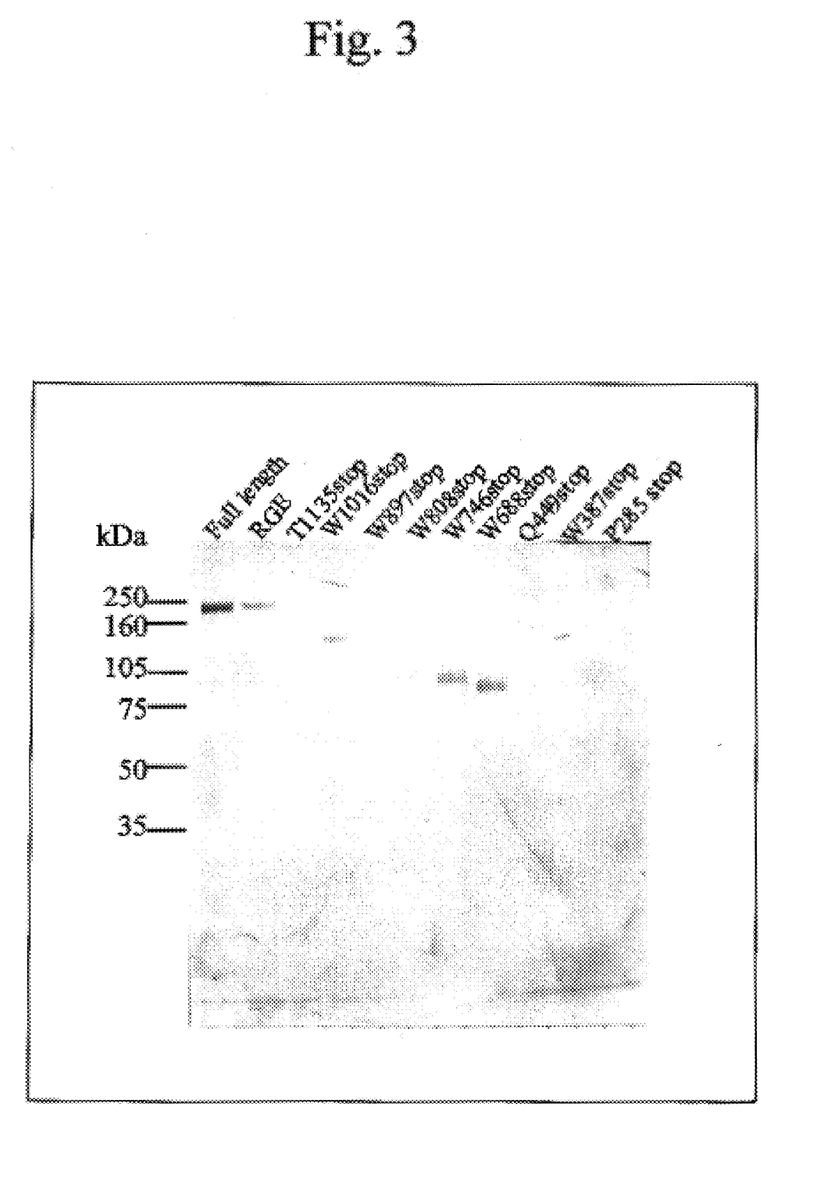
FIG. 3 is a photograph in which a region recognized by purified IgG derived from an acquired TTP patient 003 has been confirmed by Western blotting under non-reducing conditions.
Figure 4:
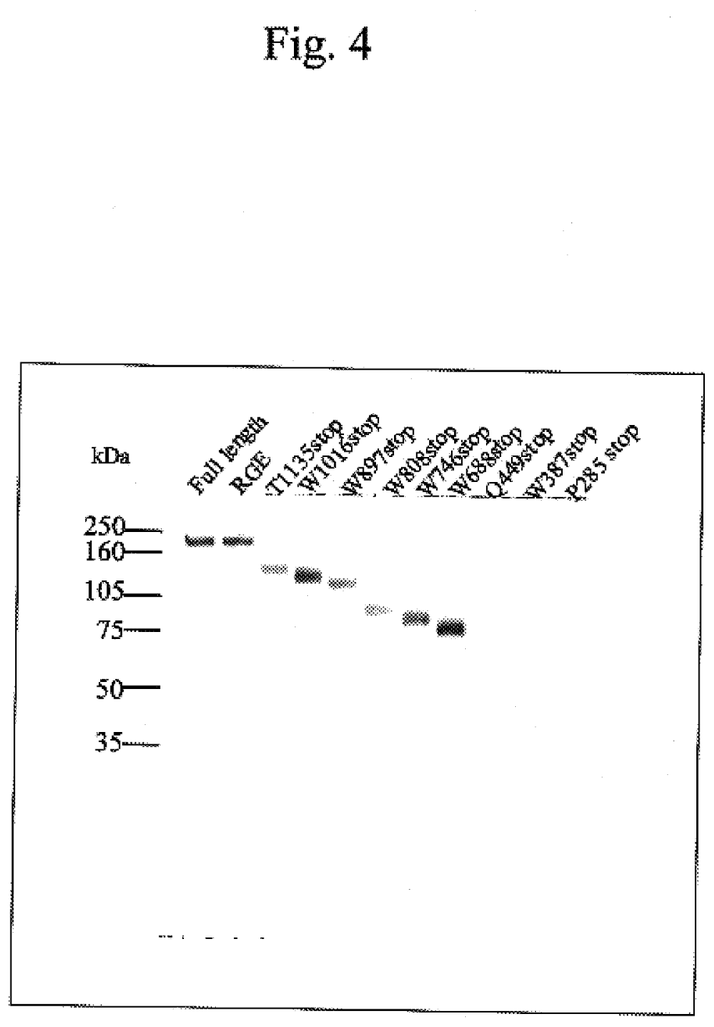
FIG. 4 is a photograph in which a region recognized by purified IgG derived from an acquired TTP patient 004 has been confirmed by Western blotting under non-reducing conditions.
Figure 5:
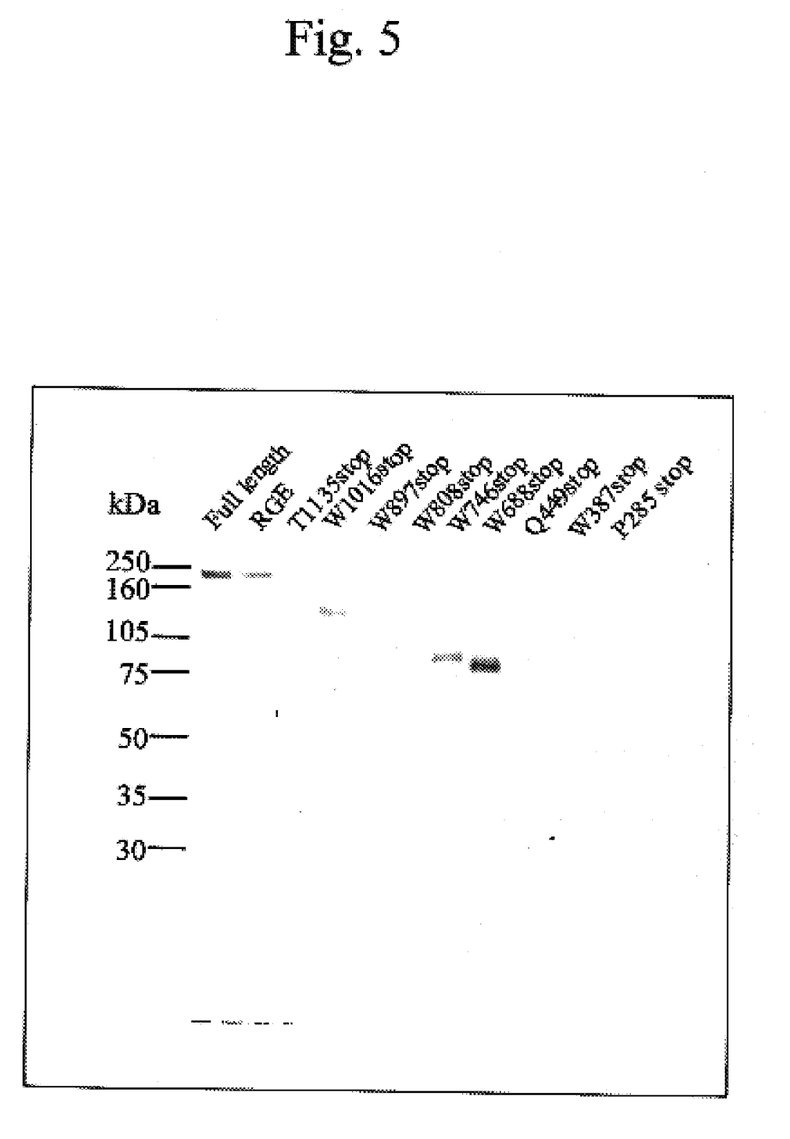
FIG. 5 is a photograph in which a region recognized by purified IgG derived from an acquired TTP patient 009 has been confirmed by Western blotting under non-reducing conditions.

IgG fractions (antibody concentration: 2 to 5 mg/ml) were prepared from plasma samples from acquired TTP patients using a protein A column according to a standard method, and diluted 200-fold to perform Western blotting. An IgG-alkaline phosphatase-labeled antibody was used as a secondary antibody in a filter, and the filter was stained with a BCIP/NBT substrate to visualize bands (FIGS. 3 to 5). The region thereby determined which is recognized by the antibody was confirmed to be located on the C-terminus side from the Q449X, because a region up to the W688X shows reactivity and a region at the Q449X shows no reactivity with all of the antibody fractions from the three patients,.

Example 2

Figure 6:
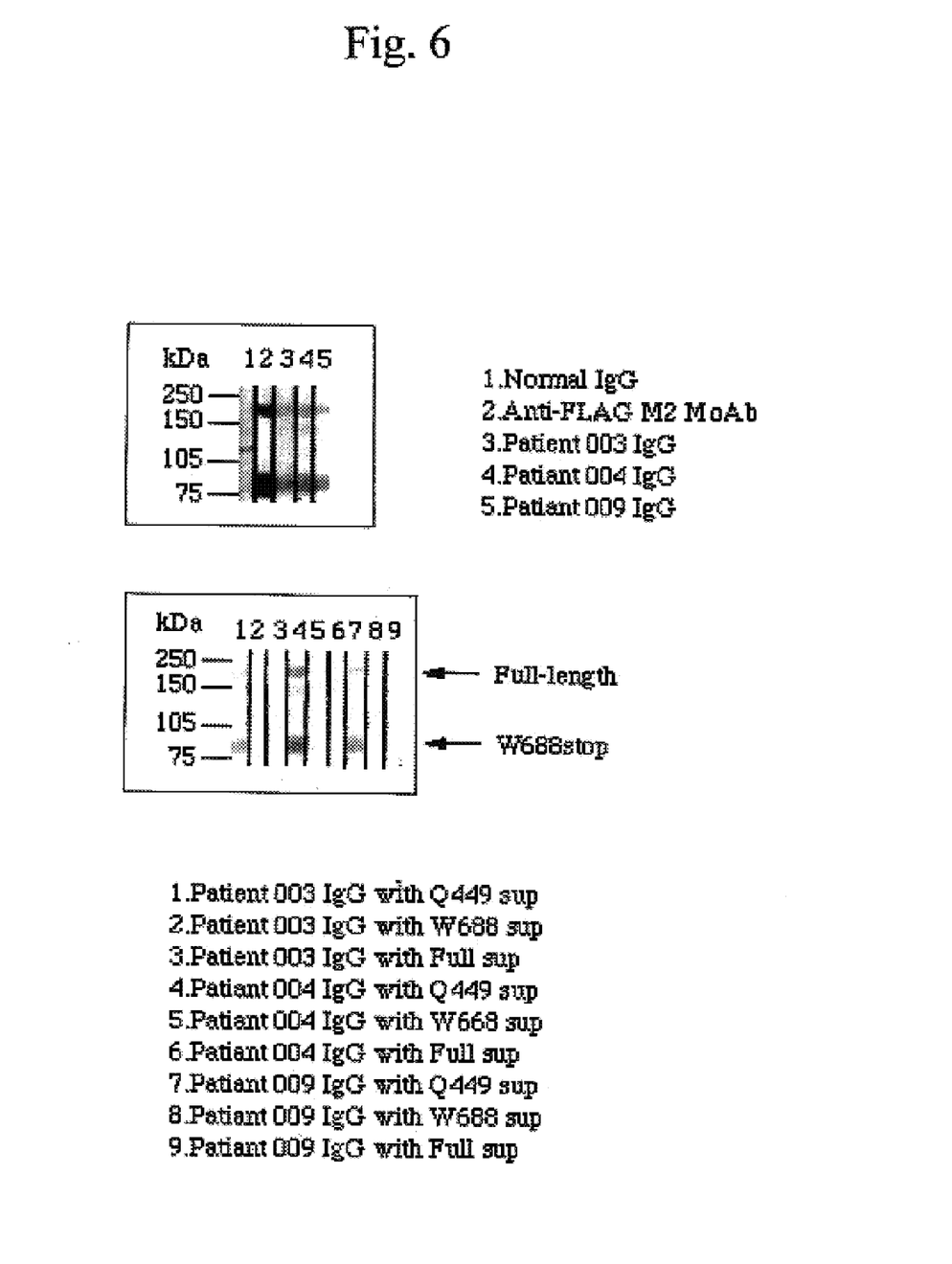
FIG. 6 is a photograph in which a more precise region recognized by purified IgG derived from the acquired TTP patients has been confirmed.

Analysis of Precise Epitope for Antibody in Acquired TTP Patient Using Western Blotting Based on Principle of Competitive Inhibition For narrowing down the more precise location of the epitope recognized by the neutralizing antibody of the present invention, supernatants from the W688X mutant and the full-length wild-type ADAMTS-13 were subjected to electrophoresis and transferred to a PVDF membrane. The PVDF membrane was utilized in a competitive inhibition system using primary antibody reaction solutions obtained by previously preincubating the above-described antibodies from the patients with a concentrated supernatant having the considerable overexpression of the Q449X mutant, the W688X mutant, or the full-length wild-type ADAMTS-13. As a result, bands positive for the full-length wild type ADAMTS-13 for all of the samples were confirmed to disappear by the W688X mutant (FIG. 6).

This has suggested that all of the antibodies from the three patients recognize a region located on the N-terminus side from the W688X.

From the results shown in Examples 1 and 2, a major neutralizing region for the autoantibodies used from the three patients was confirmed to be a region located on the terminus side of the Q449X and on the N-terminus side from the W688X, that is, a region from a Cys-rich region to a spacer region which is between the Q449X and the W688X.

All publications, patents, and patent applications cited herein are incorporated herein by reference in their entirety.

INDUSTRIAL APPLICABILITY

The findings brought about by the present invention demonstrate that a polypeptide of this invention shows specific immunoreactivity with an anti-ADAMTS-13 antibody. Therefore, the use of the polypeptide allows the rapid detection of the amount of the anti-ADAMTS-13 antibody, diagnosis for diseases associated with variations in the amount of a protease of the present invention, or the neutralization of the binding or inhibitory activity of the anti-ADAMTS-13 antibody. Thus, the polypeptide provided by the present invention provides a wide variety of applications including the detection of the anti-ADAMTS-13 antibody and other applications.

The present invention exhibits such remarkable action or effect and can be said to be an invention of great significance which contributes to every field.

The invention claimed is:

1. An isolated polypeptide consisting of the amino acid sequence from position 449 to position 687 in the amino acid sequence shown in SEQ ID NO. 1.

2. A reagent for antibody measurement comprising the polypeptide of claim 1.

3. The reagent for antibody measurement according to claim 2, wherein an autoantibody in a TTP patient is an object to be detected.

4. A composition comprising, as an active ingredient, the polypeptide of claim 1.

* * * * *

UNITED STATES PATENT AND TRADEMARK OFFICE
CERTIFICATE OF CORRECTION

PATENT NO.       : 7,572,591 B2                                              Page 1 of 1
APPLICATION NO.  : 10/549317
DATED            : August 11, 2009
INVENTOR(S)      : Soejima et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 233 days.

Signed and Sealed this

Seventh Day of September, 2010

David J. Kappos
*Director of the United States Patent and Trademark Office*